(12) United States Patent
Sathe et al.

(10) Patent No.: US 10,336,753 B2
(45) Date of Patent: Jul. 2, 2019

(54) PROCESS FOR THE PREPARATION OF APIXABAN AND INTERMEDIATES THEREOF

(71) Applicant: Unichem Laboratories Limited, Maharastra (IN)

(72) Inventors: Dhananjay G. Sathe, Maharashtra (IN); Arijit Das, West Bengal State (IN); Yashwant Surve, Maharashtra (IN); Ramdas N. Ahire, Maharashtra (IN)

(73) Assignee: Unichem Laboratories Limited, Maharastra (IN)

( * ) Notice: Subject to any disclaimer, the term of this patent is extended or adjusted under 35 U.S.C. 154(b) by 0 days.

(21) Appl. No.: 16/108,929

(22) Filed: Aug. 22, 2018

(65) Prior Publication Data

US 2018/0362528 A1     Dec. 20, 2018

Related U.S. Application Data

(60) Division of application No. 15/696,853, filed on Sep. 6, 2017, now Pat. No. 10,208,036, which is a division of application No. 15/282,373, filed on Sep. 30, 2016, now Pat. No. 9,908,881, which is a continuation-in-part of application No. PCT/IB2015/056630, filed on Sep. 1, 2015.

(30) Foreign Application Priority Data

Sep. 5, 2014 (IN) .......................... 2833/MUM/2014
Jul. 16, 2015 (IN) .......................... 2690/MUM/2015

(51) Int. Cl.
    *C07D 471/04*     (2006.01)
    *C07D 211/86*     (2006.01)

(52) U.S. Cl.
    CPC .......... *C07D 471/04* (2013.01); *C07D 211/86* (2013.01)

(58) Field of Classification Search
    CPC .................................................... C07D 471/04
    See application file for complete search history.

(56) References Cited

FOREIGN PATENT DOCUMENTS

| | | |
|---|---|---|
| CN | 101967145 | 2/2011 |
| CN | 103626689 | 3/2014 |
| EP | 3 029 028 | 6/2016 |
| WO | WO 2014/056434 | 4/2014 |

*Primary Examiner* — Paul V Ward
(74) *Attorney, Agent, or Firm* — Cesari and McKenna, LLP

(57) ABSTRACT

The present invention refers to novel process for the preparation of Apixaban. Further, the invention also related to a process for the preparation of intermediate of Apixaban from very basic and cheap row material i.e. Aniline which is widely commercially available. The present invention provides process for preparation of Apixaban using a different sequence of synthetic steps and does not involve use of Ullmann reaction.

5 Claims, 1 Drawing Sheet

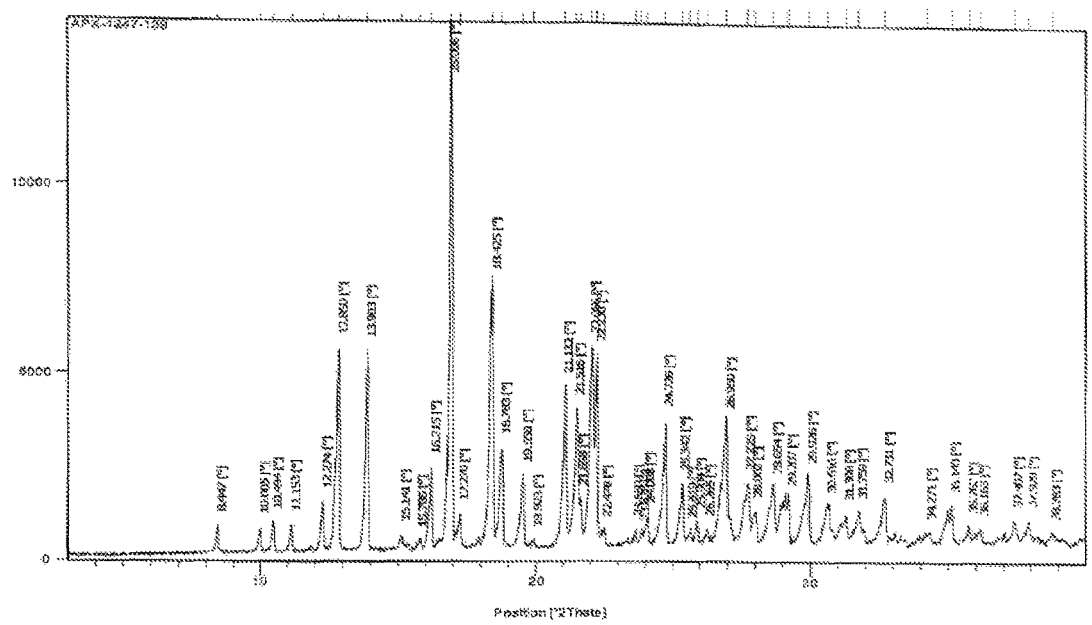

PROCESS FOR THE PREPARATION OF APIXABAN AND INTERMEDIATES THEREOF

CROSS-REFERENCE TO RELATED APPLICATIONS

This application is a divisional of U.S. application Ser. No. 15/696,853, filed Sep. 6, 2017, which is a divisional of U.S. application Ser. No. 15/282,373, filed Sep. 30, 2016, which is a continuation-in-part of International Application No. PCT/IB2015/056630, filed Sep. 1, 2015, which claims priority to Indian Application Nos. 2833/MUM/2014, filed Sep. 5, 2014, and 2690/MUM/2015, filed Jul. 16, 2015. The contents of all prior applications are hereby incorporated by reference in their entirety.

BACKGROUND

Field of Invention

The present invention is related to an improved process for the preparation of Apixaban and to a process to prepare intermediates to be used therein.

Background of the Invention

Apixaban, a factor Xa inhibitor, marketed as ELIQUIS® reduces the risk of stroke and systemic embolism in patients with nonvalvular atrial fibrillation and for the prophylaxis of deep vein thrombosis (DVT), is chemically described as 1-(4-methoxyphenyl)-7-oxo-6-[4-(2-oxopiperidin-1-yl)phenyl]-4,5,6,7-tetrahydro-1H-pyrazolo[3,4-c]pyridine-3-carboxamide i.e. compound of formula (1).

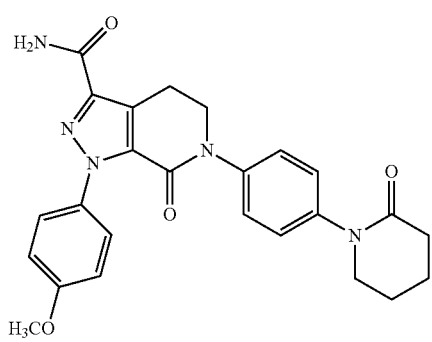

(1)

U.S. Pat. No. 6,413,980 by Bristol-Mayer first disclosed Apixaban, but is silent on process to prepare Apixaban. It is disclosed in U.S. Pat. No. 6,967,208. It teaches use of multiple bases, TEA as acid scavenger and potassium tert-butoxide as strong condensing agent to produce iodo-lactam compound of formula (4) in 81% yield which is dichlorinated with phosphoruspentachloride ($PCl_5$) in presence of chloroform to obtain morpholine compound of formula (5) in 63% yield and finally to iodo compound of formula (7) in 18% yield. Compound of formula (7) undergoes Ullmann reaction with piperidine-2-one catalyzed by copper or bivalent copper ions in presence of base at 130° C. for 24 hrs to obtain ester of compound of formula (8) followed by aminolysis in presence of ethylene glycol at 125° C. to Apixaban compound of formula (1) in 68% yield as depicted in Scheme 1.

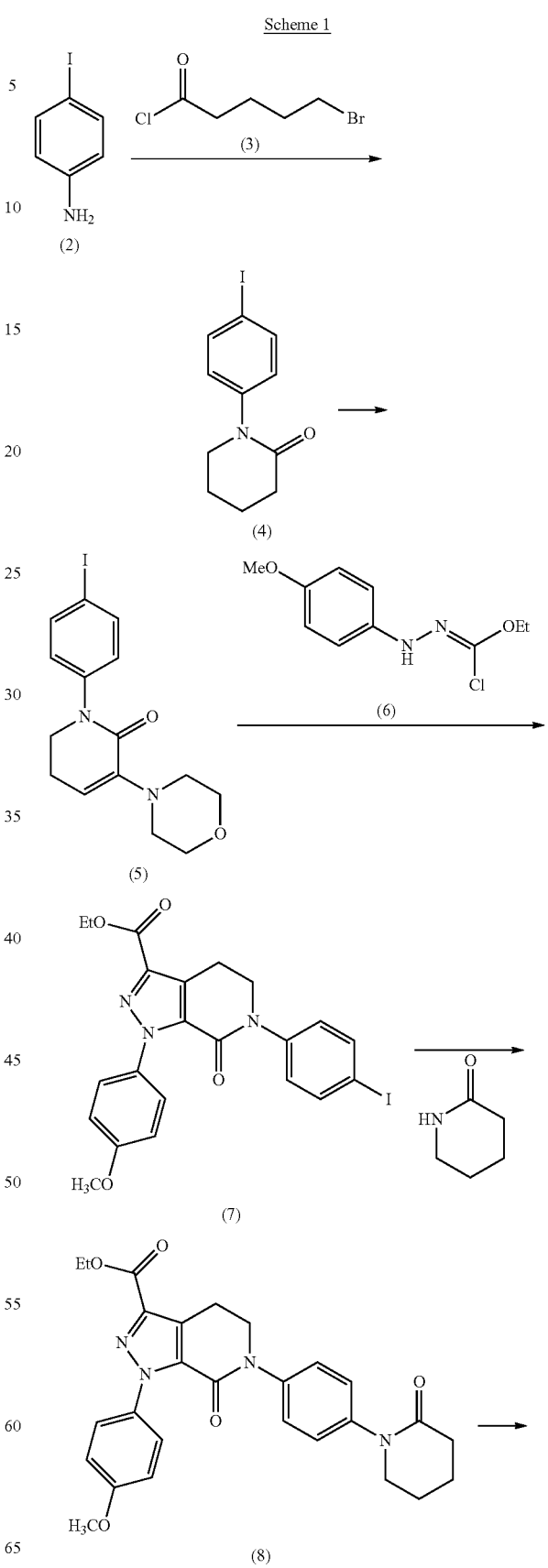

Scheme 1

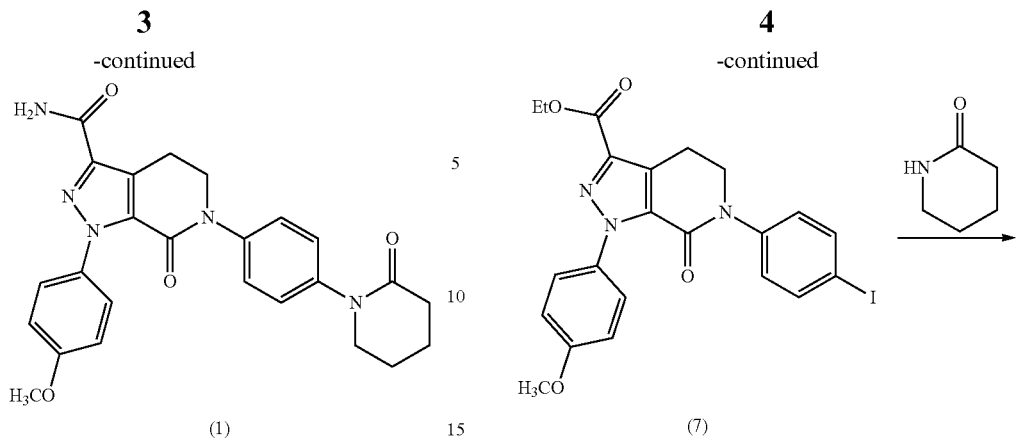

PCT application 2012/168364 described process to prepare Apixaban by reacting Para-Iodoketolactam compound of formula (19) with trimethyl silyl chloride to obtain diene compound of formula (20). On cycloaddition with hydrazono compound of formula (6), it produces iodo compound of formula (7) in 63% yield. It, on Ullmann reaction with Pipyridin-2-one in presence of Copper produces ester compound of formula (8) in 67% yield followed by aminolysis with aq. Ammonia to obtain Apixaban compound of formula (1) as shown in scheme 2.

Scheme 2

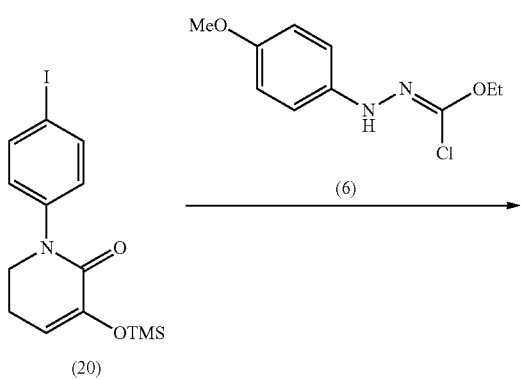

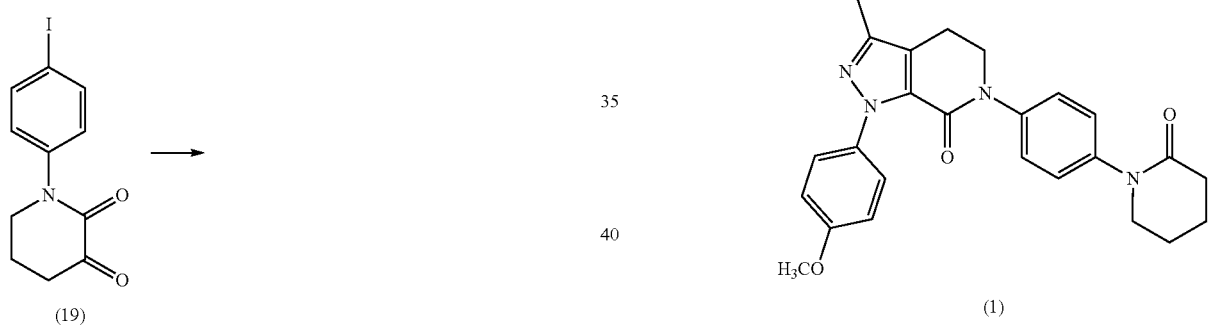

US'980 and WO'364 teach use of costly Iodo-compounds. Ullmann reaction/condensation involves use of copper besides drawbacks of harsh reaction conditions, high reaction temperature, long reaction time, high metal loading and the reaction has a reputation for erratic yields.

PCT application No. 2007/001385 discloses process to prepare of Apixaban by reacting 4-nitroaniline compound of formula (9) with compound of formula (3) in presence of $K_2CO_3$/KOH in the mixture of THF and chlorobenzene to obtain nitrolactam compound of formula (10). It, on dichlorination with $PCl_5$ produces dichloro compound of formula (11). On dehydrohalogenation in presence of lithium carbonate, it produced mono chloro intermediate compound of formula (12). It, on reaction with hydrazono compound of formula (6) produced compound of formula (13). It is reduced to compound of formula (14) in presence of Pd/C in THF. It's reaction with, compound of formula (3) produces compound of formula (15). On cyclization and aminolysis with ammonia in presence of propylene glycol it produces Apixaban compound of formula (1) as depicted in Scheme 3.

Scheme 3

WO'385 discloses use of expensive compound of formula (3), uses mixture of chlorobenzene and THF during chlorination of compound of formula (10) with PCl₅. Work up procedure for isolation of compound of formula (11) is tedious and required expensive and hygroscopic strong base such as potassium ethoxide for the cyclization of compound of formula (15).

Synthetic communication, 2013, 43, 72-79 disclosed preparation of Apixaban using key intermediate compound of formula (18). The starting material 4-nitroaniline compound of formula (9) is reacted with compound of formula (3) in presence of triethyl amine/THF and cyclization is carried out in presence of potassium tert-butoxide to obtain compound of formula (10) which on chlorination with PCl₅, followed by the condensation-elimination process with excessive morpholine produced nitro-morpholine compound of formula (16) in 78% yield followed by reduction of nitro group in presence of sodium sulfide to obtain aniline-morpholine compound of formula (17). Similarly second acylation/cyclization of compound of formula (17) with compound of formula (3') in two steps, produced key intermediate having lactam compound of formula (18), wherein acylation is carried out in presence of triethyl amine/THF and cyclization is carried out in presence of potassium tert-butoxide. The compound of formula (18) is reacted with hydrazono compound of formula (6) to obtain ester compound of formula (8) which by aminolysis in methanolic ammonia solution produced Apixaban compound of formula (1) as depicted in Scheme 4.

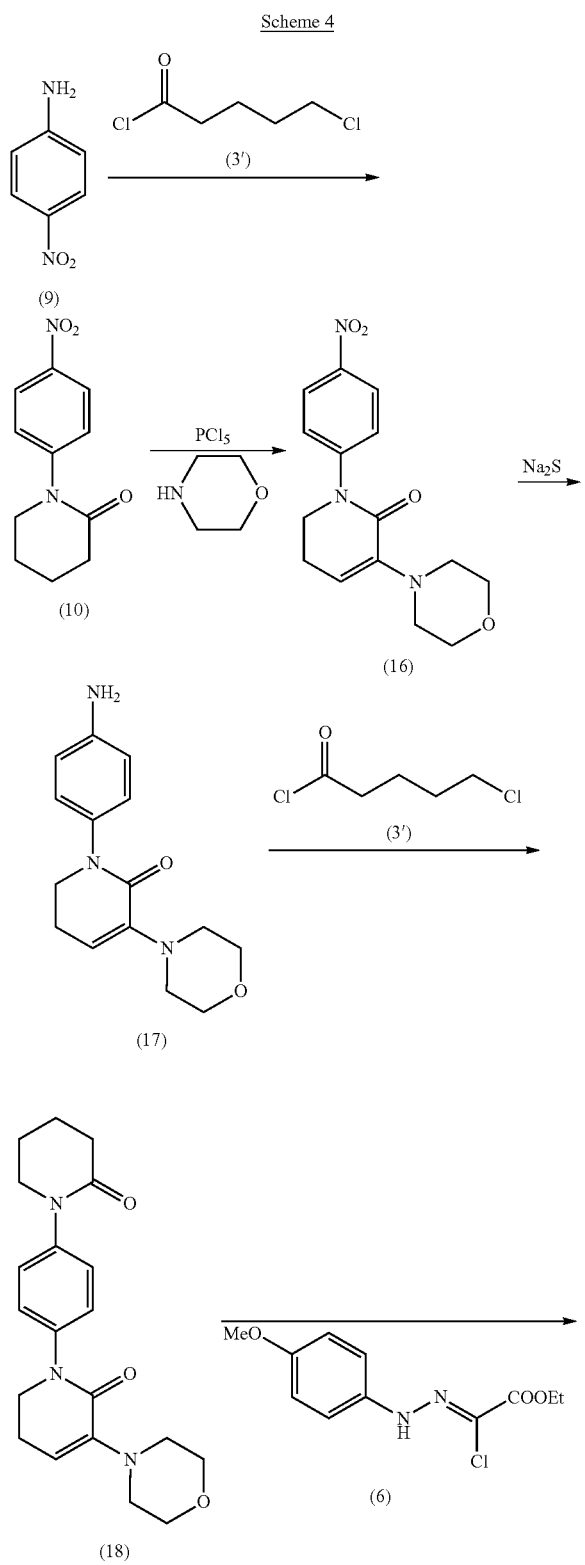

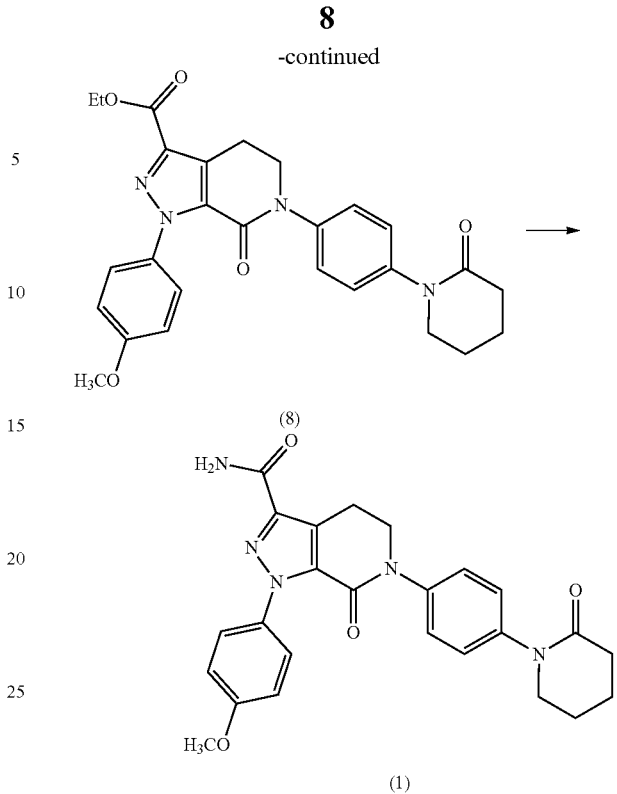

Above non-patent literature discloses the use of TEA as an acid scavenger in the acylation reaction and then potassium tert-butoxide as a strong condensing agent in the subsequent cyclization during the preparation of compound of formula (10) and (18). It uses large volume of THF for preparation of (10) and (18) and Potassium tert-butoxide is hygroscopic, corrosive in nature. The chlorination of compound of formula (10) requires overall 25 volumes of chloroform with $PCl_5$. which is undesirable. It uses $Na_2S$, a potential environmentally hazardous compound for the reduction of nitro group. The reaction uses TEA and Potassium tert-butoxide in one pot acylation/cyclization sequence to prepare compound of formula (10) and (18). The overall process is costly.

CN 103626689 patent application discloses the reaction of aniline with compound of formula (3') in presence of organic base in organic solvent to obtain compound of formula (24), which is then reacted with inorganic base to obtain compound of formula (21). Nitrating compound of formula (21) by conc. sulfuric acid and nitric acid produces compound of formula (10). The process to prepare (21) needs with two bases, organic base for acylation and inorganic base for cyclization. This multiplied material requirement has disadvantages associated with it. Reported yields in some stages are poor and it is silent on purity aspects.

U.S. Pat. No. 7,396,932 discloses complicated process to prepare the Apixaban N-1 crystalline form and H2-2 crystalline form.

US'980 disclosed the aminolysis of compound of formula (8) in presence of ammonia in ethylene glycol. Whereas WO'364 and Syn. Comm. 2013 disclosed aminolysis in aqueous ammonia in MeOH which produces acid impurity (8a). The acid impurity (8a) directly effect on yield of the final product and also involves extra purification process.

Above prior arts disclosed the use of expensive nitro aniline compound for the preparation of compound of formula (10).

9

Various processes are disclosed in CN101967145, CN102675314 and WO2013119328 for the preparation of Apixaban which are quite complicated.

In view of prior art methods available for the preparation Apixaban and its intermediates, there is a need for simple and cost effective processes as well as industrial and environmental friendly improved process for preparing Apixaban. Industry needs a simpler process that uses relatively inexpensive starting materials to provide significant economic advantages yet produces Apixaban in high yield.

OBJECT OF THE INVENTION

The main object of the invention is to provide a simple and improved process to prepare Apixaban starting from Aniline and the intermediates required in the process.

Another object of the invention is to provide the process to prepare intermediate compounds of the formula (21), (25), (10), amino-morpholine compound of the formula (17) and intermediate lactam compound of the formula (18).

Yet another object of the invention is to provide the improved process for the preparation of Apixaban from compound of formula (8).

Yet another object of the invention is to provide the novel processes to prepare the N-1 crystalline form of Apixaban.

The present invention is to provide a process for the preparation of Apixaban which overcomes the problems of the prior art.

Yet another object of the present invention is to provide a process to prepare Apixaban compound of formula (1) with high yields and which can be carried out under milder conditions.

Yet another object of the invention is to provide industrially scalable, cost effective, environment friendly and robust process for the preparation of Apixaban and intermediates thereof.

SUMMARY OF THE INVENTION

The invention provides a simple and improved process to prepare Apixaban from starting from Aniline and the intermediates required in the process.

Accordingly provided process to prepare compound of the formula (21) comprising steps of;

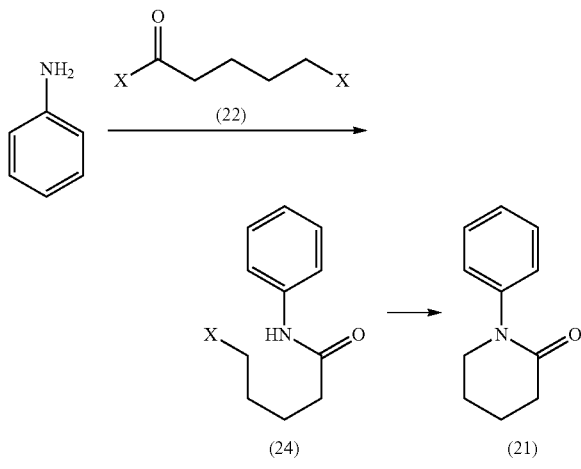

a. reacting aniline with compound of formula (22) in presence of inorganic base or aqueous solution of inorganic base or absence of any base to obtain compound of formula (24) wherein X is leaving group;
b. optionally isolating the compound of formula (24);
c. cyclizing compound of formula (24) in presence of inorganic base or aqueous solution of inorganic base to obtain compound of formula (21).

The invention provides a single step process to prepare compound of the formula (10) comprising steps of;

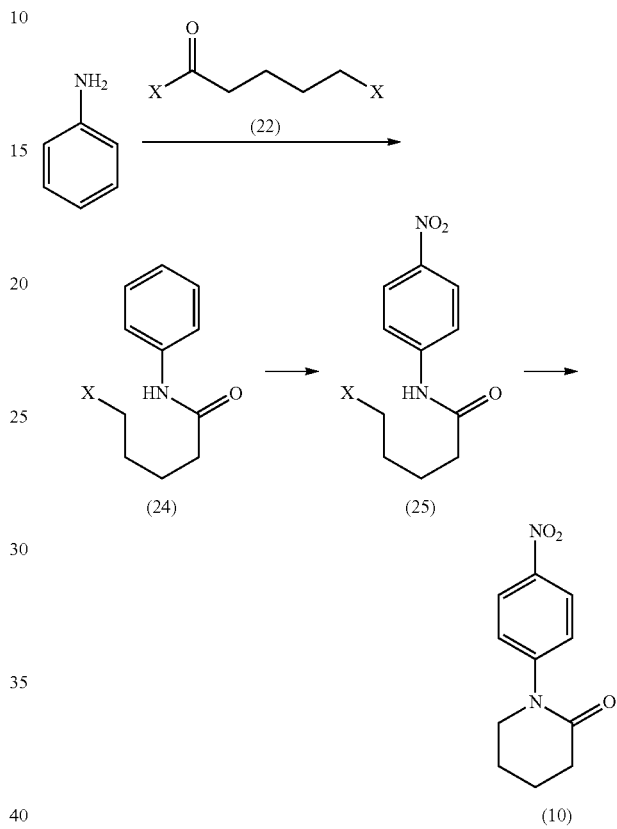

a. reacting aniline with compound of formula (22) in presence of inorganic base or aqueous solution of inorganic base or absence of any base to obtain compound of formula (24) wherein X is leaving group;
b. optionally isolating the compound of formula (24);
c. nitrating compound of formula (24) to obtain compound of formula (25) using Nitric acid in Sulphuric acid or Acetic acid;
d. optionally isolating the compound of formula (25);
e. cyclizing compound of formula (25) in presence of inorganic base or aqueous solution of inorganic base to obtain compound of formula (10).

According to another aspect of the invention is provided the process to prepare amino-morpholine compound of the formula (17) comprising steps of:
a. reacting a compound of formula (10) with chlorinating agent in presence of non-halogenated solvent to obtain compound of formula (11);
b. reacting compound of formula (11) with morpholine optionally in presence solvent to obtain nitro-morpholine of formula (16);
c. optionally isolating and purifying the nitro-morpholine of formula (16);
d. reducing nitro-morpholine of formula (16) in presence of a hydrazine hydrate with catalytic amount of Raney Nickel to obtain compound of formula (17).

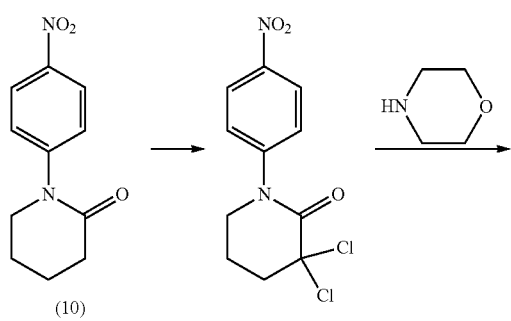

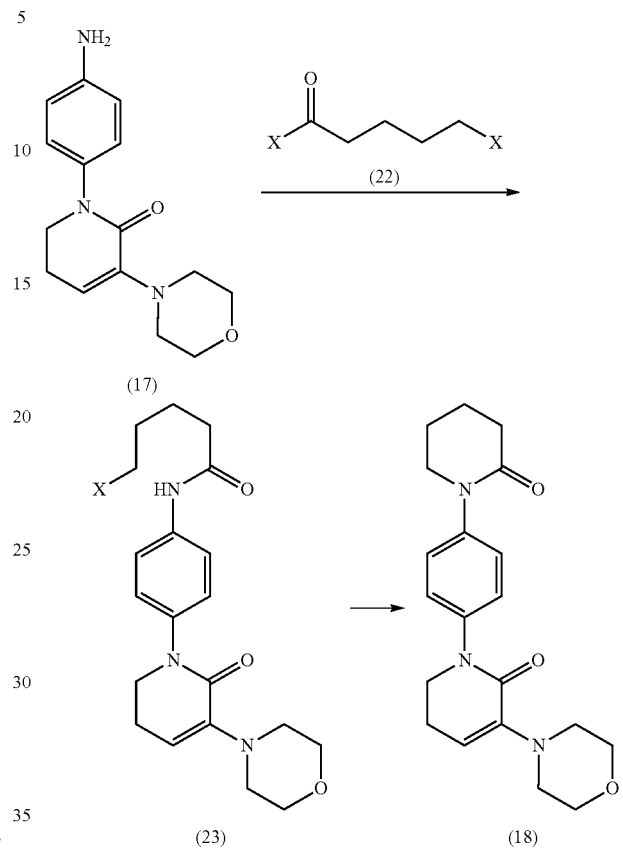

c. cyclizing amide-compound of formula (23) in presence of inorganic base or aqueous solution of inorganic base to obtain a lactam compound of formula (18).

According to another aspect of the invention is provided the single step process to prepare compound of formula (18) comprising steps of;
a. reacting amino-morpholine compound of formula (17) with compound of formula (22) in presence of inorganic base or aqueous solution of inorganic base or absence of any base to obtain amide-compound of formula (23) wherein X is leaving group;
b. optionally isolating the amide-compound of formula (23);

According to one aspect of the invention is provided the process to prepare Apixaban.

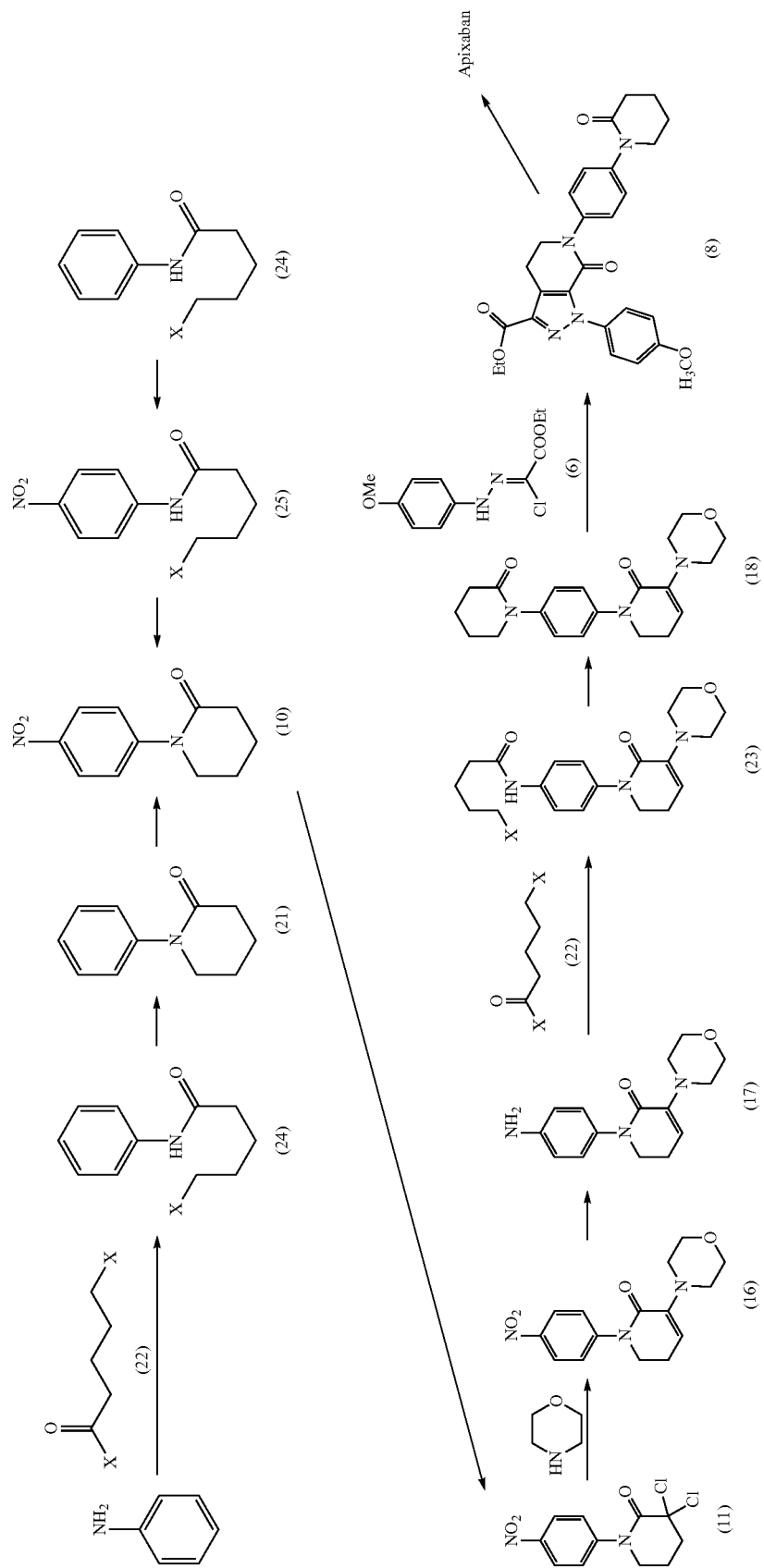

According to another aspect of the invention is provided an improved process for the preparation of Apixaban from compound of formula (8) to control the formation of acid impurity (8a).

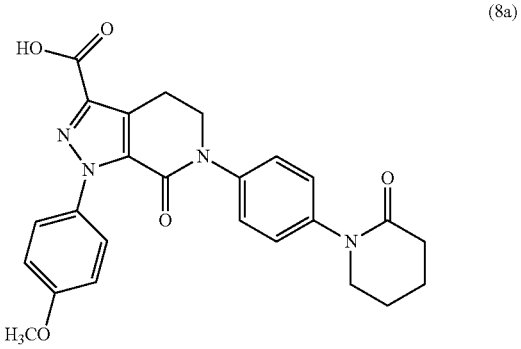 [SMILES: COc1ccc(-n2nc(C(=O)O)c3c2C(=O)N(c2ccc(N4CCCCC4=O)cc2)CC3)cc1]

(8a)

According to another aspect of the invention is provided a novel processes for preparation of N-1 crystalline form of Apixaban.

BRIEF DESCRIPTION OF THE DRAWING

The description below refers to the accompanying drawing, in which:

FIG. 1 is an XRPD profile of N-1 crystalline form of Apixaban of formula (I).

DETAILED DESCRIPTION OF THE INVENTION

The invention mainly provides simple and improved process to prepare Apixaban starting from Aniline and the intermediates required in the process.

According to another aspect of the invention, there is provided an improved process to prepare compound of the formula (21) comprising steps of:

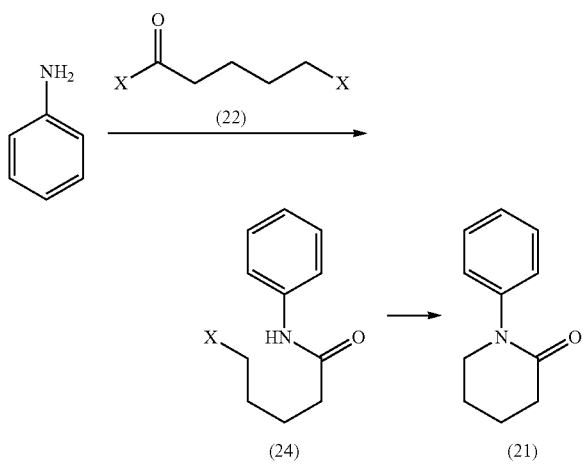

a. reacting aniline with compound of formula (22) in presence of inorganic base or aqueous solution of inorganic base or absence of any base to obtain compound of formula (24) wherein X is leaving group;
b. optionally isolating the compound of formula (24);
c. cyclizing compound of formula (24) in presence of inorganic base or aqueous solution of inorganic base to obtain compound of formula (21);

The compound of formula (22) is selected from bromovalerylchloride (BVC) or chlorovalerychloride (CVC), more preferably chlorovaleryl chloride.

The example of leaving group may include but not limited Cl, Br, I, F, methane sulfate, mesylate, triflate, tosylate and tert-butyldimethylsilyloxy group.

The inorganic base used in step a) and step c) is selected from sodium carbonate, potassium carbonate, lithium carbonate, lithium hydroxide, sodium hydroxide (NaOH), potassium hydroxide (KOH), ammonium hydroxide, lithium hydrate, potassium hydrate, sodium hydrate, lithium hydrogen carbonate, sodium hydrogen carbonate, potassium hydrogen carbonate or aqueous solution thereof and mixture(s) thereof. Preferred base used is KOH or NaOH. Hereafter the term any base includes organic or inorganic base.

The reaction in step a) and step c) can be conveniently carried out in presence of a solvent. The example of solvent in step a) and step c) may include but not limited to dichloromethane (MDC), ethyl acetate (EtOAc), methyl acetate, $CHCl_3$, toluene, chlorobenzene, dimethylformamide (DMF), dimethylacetamide, N-methylpyrrolidone, acetonitrile, dimethyl sulfoxide, tetrahydrofuran (THF), dioxane, ethanol (EtOH), methanol (MeOH) and mixture(s) thereof, preferably used are DMF or MDC.

In step a) reaction of aniline with compound of formula (22) is carried out without using any base i.e. in absence of any base to provide compound of formula (24).

The reaction in step a) and step c) can be conveniently and optionally carried out in presence of a phase transfer catalyst. The examples of phase transfer catalyst is selected from quaternary ammonium and phosphonium salts such as methyltridecyl ammonium chloride, trimethyl ammonium chloride, tetrabutyl ammonium bromide, dimethylethylhexadecyl ammonium bromide, ethyltripentyl ammonium iodide, hexadecyltributylphosphonium bromide benzyl trimethyl ammonium chloride, and the like.

The reaction is successfully carried out optionally isolating compound of the formula (24) and can be isolated by method known in the art such as cooling, filtration, centrifugation, washing, drying and combination thereof.

The molar equivalent of halovalerylhalide used in step a) from 1.0, 1.05, 1.1, 1.25, 1.35, to 1.5 equivalents, preferably between 1.1 to 1.5 equivalents and more preferably between 1.1 to 1.2 equivalents.

The molar equivalent of base used in step a) from 0.5, 0.6, 0.7, 0.8, 0.9, 1.0, 1.1, 1.2, 1.3, 1.4 to 1.5 and in step c) from 2.0, 2.5, 3.0, 3.5 to 4.0, more preferably 3.0 equivalents.

The reaction of step a) and c) is performed preferably in a temperature range between 0° C. to ambient temperature.

Inventive step of the present invention resides in use of single inorganic base or in the absence of the base as against two bases (organic and inorganic) used in CN 103626689. Inherent limitations of CN 103626689 forced the use of inorganic base in next part of reaction, as is evident from the claim 1. Prior art discloses acylation/cyclization reaction in presence of multiple bases such as TEA and potassium tert-butoxide which is hygroscopic and corrosive in nature. In the present invention acylation/cyclization reaction for the preparation of compound of formula (21) is performed in the presence of single inorganic base or aqueous solution of inorganic base such as KOH instead of use of multiple bases. Further, the inventive step resides not only in improved purity and better yields but also in flexibility to use more than one inorganic base to carry out the same reaction.

Prior art teaches or discloses reaction of Aniline with compound of the formula (22) in presence of base. Inventive step of the present invention also resides in reaction of the Aniline with compound of formula (22) without using base.

Present invention provides a cleaner method free of tedious and cumbersome procedures for isolation of product. Surprisingly the yields of acylation and cyclization are far better than the yields disclosed by CN 103626689.

According to one aspect of the invention is provided the single step process to prepare compound of the formula (10) comprising steps of;

a. reacting aniline with compound of formula (22) in presence of inorganic base or aqueous solution of inorganic base or absence of any base to obtain compound of formula (24) wherein X is leaving group;
b. optionally isolating the compound of formula (24);
c. nitrating compound of formula (24) to obtain compound of formula (25) in presence of Nitric acid in Sulphuric acid or Acetic acid;
d. optionally isolating the compound of formula (25);
e. cyclizing compound of formula (25) in presence of inorganic base or aqueous solution of inorganic base to obtain compound of formula (10).

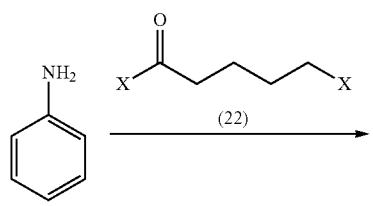

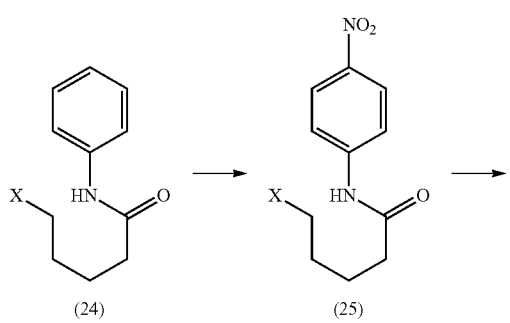

The preparation of compound of formula (24) is carried out as described above.

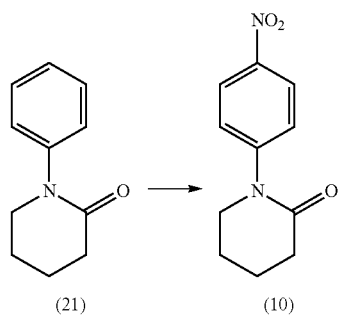 [SMILES: O=C1CCCCN1c1ccccc1 ; O=C1CCCCN1c1ccc([N+](=O)[O-])cc1]

The nitration of compound of formula (21) and (24) are carried out with a nitrating agent, such as nitric acid in presence of sulfuric acid or acetic acid. The molar equivalent of nitrating agent used is from 0.9. 1.0. 1.05 0.9, 1.0 1.05, 1.1 to 1.2, more preferably 1.05 equivalents. The amount of sulfuric acid used from 1.0, 1.2, 1.3, 1.5, 1.8 to 2.0 Vol wrt the compound of formula (21) and (24) accordingly, preferred being 1.6 Vol. The nitration of compound of formula (21) and (24) can be performed in a temperature between −10° C. to ambient temperature, more preferably at temperature in between −5° C. to 10° C.

Present invention provides a simple and cost effective process for the preparation of compound of formula (10) by using very cheap aniline as starting material as compared to expensive nitro aniline described in prior art. The reaction is successfully carried out optionally isolating compound of the formula (24) and (25). Isolation of compound of formula (24) and (25) can be carried out by any method known in the art such as cooling, filtration, centrifugation, washing, drying and combination thereof. Cyclisation of compound of formula (25) is carried out under same reaction conditions as used for cyclizing compound of formula (24).

Another aspect of the present invention is to provide a process for the preparation of amino-morpholine compound of formula (17) comprising steps of:

a. reacting a compound of formula (10) with chlorinating agent in presence of non-halogenated solvent to obtain compound of formula (11);
b. reacting compound of formula (11) with morpholine optionally in presence solvent to obtain nitro-morpholine of formula (16);
c. optionally isolating and purifying the nitro-morpholine of formula (16);
d. reducing nitro-morpholine of formula (16) in presence of a hydrazine hydrate with catalytic amount of Raney Nickel to obtain compound of formula (17).

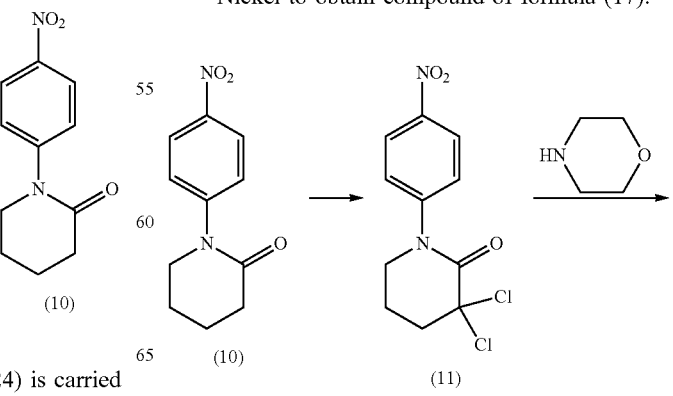

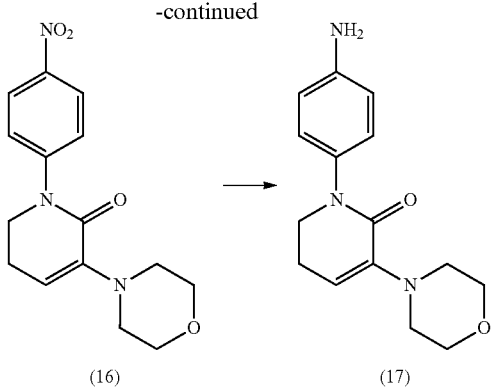

(16) (17)

Inventive step of the invention also resides in use of non halogenated solvents and mixtures thereof in step a) as shown in one preferred embodiment of the invention, the chlorination of compound of formula (10) in step a).

Chlorinating agents selected from group consisting of thionyl chloride ($SOCl_2$), phosphorous trichloride ($PCl_3$) or $PCl_5$. The molar equivalent of chlorinating agent used from 2.5, 2.7, 2.9, 3.0, 3.2, 3.4, to 3.5 more preferably 3.0 equivalents. The said chlorination can be performed in a temperature between 45° C. to 90° C. more preferably at temperature 65° C.-75° C.

Non limiting examples of non-halogenated solvents include toluene, xylene, benzene, acetic acid, ethyl acetate, tetrahydrofuran, methyl t-butyl ether, methyl ethyl ketone; dioxane and mixture(s) thereof preferably used toluene.

The nitro-morpholine compound of formula (16) of step b) is obtained by simultaneous condensation-elimination reaction with excess of morpholine with compound of formula (11). The excess of morpholine used from 2.0, 3.0, 4.0 to 5.0 volumes, more preferably 2.0 to 3.0 volumes wrt the compound of formula (11). The reaction can be performed at a temperature 90° C. to 130° C.

The process for the preparation of nitro-morpholine of formula (16) involves exothermic reaction of dissolving compound of formula (11) in morpholine and refluxing it. Present invention minimizes exothermic reaction using solvent and morpholine in preparation of nitro-morpholine.

The solvent used in step (b) may include N-Methyl-2-pyrrolidone or DMF. The morpholine is used from 2.0, 3.0, and 4.0 to 5.0 volumes, more preferably 1.5 to 2.0 volumes wrt the compound of formula (11).

The reaction can be performed at a temperature 60° C. to 130° C. The obtained product can be optionally recrystallized in presence of suitable solvent selected from the group of alcohols, ketones, esters, ethers, nitriles and mixture(s) thereof, preferably MeOH.

The amino-morpholine compound of formula (17) of step d) is obtained by reducing nitro-morpholine compound of formula (16).

Prior art disclose the reduction of nitro group of compound of formula (16) in presence of potentially environmentally hazardous $Na_2S$, in the presence of expensive metals like palladium, platinum, ruthenium etc. and requires precautions, due to their flammable nature in the air. It also required highly diffusible and flammable compressed hydrogen gas, besides reflux temperatures and longer hours. Procedures of prior art are complicated. Present invention is devoid of $Na_2S$.

Present invention reduces of nitro group of nitro-morpholine by drop wise addition of hydrazine hydrate to the solution of nitro-morpholine, EtOH, water and catalytic amount of Raney Nickel at temperature in between 50° C. to 75° C.

Solvent is selected from water, isopropyl alcohol (IPA), EtOH, MeOH, n-propanol or aq. solution thereof and mixture(s) thereof or aqueous solutions thereof.

The molar equivalent of hydrogenating agent is used from 2.0, 3.0, 4.0, 5.0, to 6.0 equivalents more preferably 4.0 mole equivalent. The mole ratio of catalyst includes 2%, 3%, 4% to 5% more preferably around 4%.

Another aspect of the present invention is to provide a single step process for the preparation of intermediate lactam compound of formula (18) comprising steps of:
a. reacting amino-morpholine compound of formula (17) with compound of formula (22) in presence of inorganic base or aqueous solution of inorganic base or absence of any base to obtain amide-compound of formula (23) wherein X is leaving group;
b. optionally isolating the amide-compound of formula (23);
c. cyclizing amide-compound of formula (23) in presence of inorganic base or aqueous solution of inorganic base to obtain a lactam compound of formula (18).

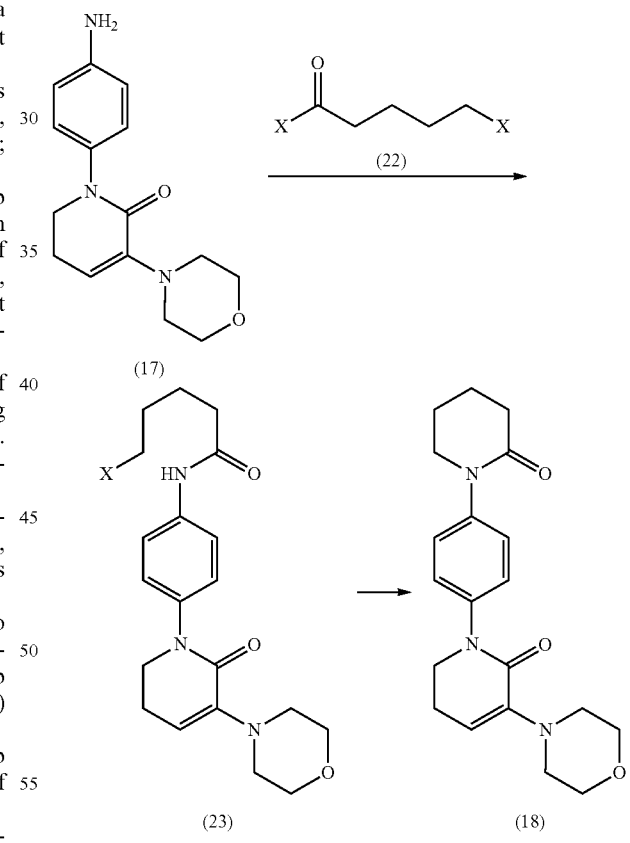

(23) (18)

Inventive step resides in using single base to complete the reaction. The reaction is successfully carried out with or without the isolation of compound of the formula (23). This is strikingly different from the prior art where in multiple solvents are used in addition to use of base e.g. Synthetic communication, Jian'an Jiang 2013, 43, 72-79. Inherent limitations of these disclosures necessitate use of multiple hygroscopic and corrosive bases. Inventive step of the present invention resides in the use of single inorganic base or aqueous solution of inorganic base, achieves acylation and cyclization and thereby eliminates disadvantages of material procurement, inventories besides technical drawbacks. Further, invention disclosed in the present invention provides flexibility to use more than 1 inorganic base.

The non-limiting examples of inorganic base used in step a) and step c) include sodium carbonate, potassium carbonate, lithium carbonate, lithium hydroxide, NaOH, KOH, ammonium hydroxide, lithium hydrate, potassium hydrate, sodium hydrate, lithium hydrogen carbonate, sodium hydrogen carbonate, potassium hydrogen carbonate or aqueous solution of inorganic bases and mixture(s) thereof. Preferred base used is KOH.

The example of leaving group may include but not limited Cl, Br, I, F or methane sulfate, mesylate, triflate, tosylate and tert-butyldimethylsilyloxy group.

The reaction in step a) wherein reaction of amino-morpholine compound of formula (17) with compound of formula (22) is carried out without using any base i.e. in absence of any base to provide compound of formula (23).

The reaction in step a) and step c) is conveniently carried out in presence of a solvent. Non limiting examples of solvent in step a) and step c) include MDC, toluene, ethyl acetate, methyl acetate, CHCl$_3$, chlorobenzene, DMF, dimethylacetamide, N-methylpyroolidone, acetonitrile, dimethyl sulfoxide, THF, dioxane and mixture(s) thereof, preferred are DMF or MDC.

The reaction in step a) and step c) can be conveniently and optionally carried out in presence of a phase transfer catalyst. The examples of phase transfer catalyst mat include quaternary ammonium and phosphonium salts such as methyltridecyl ammonium chloride, methyltridecyl ammonium chloride, trimethyl ammonium chloride, tetrabutyl ammonium bromide, dimethylethylhexadecyl ammonium bromide, ethyltripentyl ammonium iodide, benzyltrimethylammoniumchloride, hexadecyltributylphosphonium bromide and the like.

The molar equivalent of compound of formula (22) used in step a) from 1.0, 1.05, 1.1, 1.25, 1.35, to 1.5 equivalents, preferably between 1.1 to 1.5 equivalents and more preferably between 1.1 to 1.2 equivalents.

The molar equivalent of base used in step a) from 0.5, 0.6, 0.7, 0.8, 0.9, 1.0, 1.1, 1.2, 1.3, 1.4 to 1.5 and in step c) from 2.0, 2.5, 3.0, 3.5 to 4.0, more preferably 3.0 equivalents.

The reaction of step a) and b) is can be performed preferably in a temperature between 0° C. to ambient temperature.

According to the present invention acylation/cyclization reaction for the preparation of compound of formula (18) can be performed in the presence of single inorganic base such as KOH.

The said amide compound of formula (23) can be converted in-situ to the lactam compound of formula (18). This simultaneous amide and lactam formation can be achieved with base in a solvent. The example of base may include KOH, NaOH, and lithium hydroxide, more preferably NaOH and KOH. The example of solvent may include THF, DMF, dimethyl acetamide, CHCl$_3$, chlorobenzene, toluene, MDC, water and the like or mixture(s) thereof or aqueous solution thereof, preferably aqueous solution of MDC.

During formation of the lactam compound of formula (18); amide-compound of formula (23) can be optionally isolated and purified by common purification processes such as recrystallization, leaching or slurry washing, or by co-precipitation with a suitable solvent(s) and anti-solvent(s). The solvent essentially refers to a media in which is compound is readily soluble and the anti-solvent essentially refers to a media in which is compound is insoluble or poorly soluble.

The amount of solvent used is from about 5 vol to about 15 vol with respect to compound of formula (17) and said reaction can be performed in a temperature between 5° C. to 35° C., more preferably at temperature between 10° C. 30° C.

Preparation of Hydrazono Compound of Formula (6):

The process for the preparation of hydrazono compound of formula (6) comprising reacting p-anisidine with sodium nitrite and hydrochloric acid, followed by reaction with ethyl-2-chloroacetoacetate it is well known in the art.

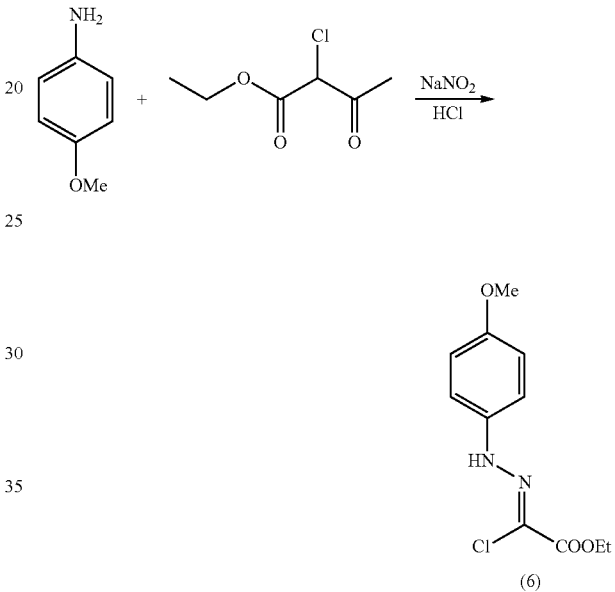

Preparation of Ester Compound of Formula (8):

The 1,3-cycloaddition involves reaction of hydrazono compound of formula (6) with lactam compound of formula (18) in presence of a solvent and base at ambient temperature to reflux temperature to obtain ester compound of formula (8).

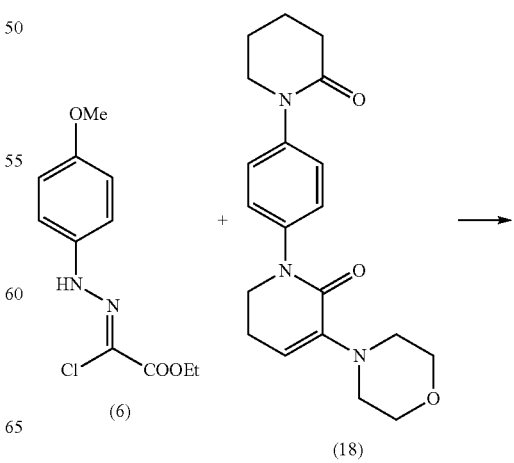

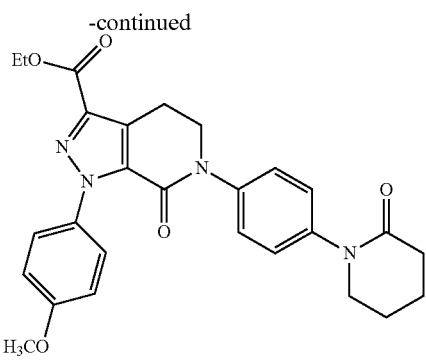

(8)

The example of solvents may include but not limited to ethyl acetate, dichloromethane, tetrahydrofuran, acetonitrile and mixture(s) thereof. The examples of base may include triethyl amine, diisopropylethylamine and the like at temperature between 0° C. to ambient more preferably at room temperature.

Preparation of Apixaban:

Another aspect of the present invention is to provide improved process for the preparation of Apixaban compound of formula (1) by aminolysis of compound of formula (8) in anhydrous Methanolic ammonia. The aminolysis of carried out at temperature range between 60° C. to 70° C. in a closed autoclave condition.

Another aspect of the present invention is to provide reaction of compound of formula (8) with ammonia at temperature between 40° C. to 65° C. in a closed autoclave condition. Further the present invention provides a novel process for the preparation of N-1 crystalline form of Apixaban comprising steps of;
 a. dissolving apixaban in mixture of MeOH and DMF;
 b. optionally heating the solution at temperature range of 60° C. to 70° C.;
 c. recovering N-1 crystalline form of Apixaban.

Further aspect of the present invention is to provide another process for the preparation N-1 crystalline form of Apixaban comprising steps of;
 a. dissolving Apixaban in polar solvent;
 b. optionally heating the solution at temperature range of 60° C. to 80° C.;
 c. add water to the solution;
 d. recovering N-1 crystalline form of Apixaban.

The example of polar solvent includes but not limited to alcohols, amides and sulfoxides or mixture(s) thereof. The examples of alcoholic solvents may include MeOH, EtOH, propanol, 1,2-propylene glycol, chlorobutanol. The example of amide solvents may include DMF, diethylformamide, dimethylacetamide, N-methylpyrrolidone. The example of sulfoxide may include dimethyl sulfoxide.

The present invention provides a process for purification of Apixaban wherein apixaban is dissolved in DMF and water is added as an anti-solvent.

The present invention provides a process for preparation of Apixaban wherein the compound of formula (8), imp-A and imp-6 is less than 0.1% w/w of Apixaban, as measured by HPLC (high performance liquid chromatography).

The product is isolated by conventional means e.g. either direct filtration of the solid product or addition of antisolvent followed by filtration of the product, or complete or partial solvent evaporation and recovering the product.

The obtained product can optionally be purified by conventional means, such as recrystallization from a suitable solvent or mixture(s) of solvents, recrystallization using solvent-anti-solvent mixture(s), reslurrying in solvent or mixture(s) of solvent, treatment with a base or an acid.

Apixaban N-1 form can be recovered by one of the known techniques, such as filtration or centrifugation, preferably filtration.

In following examples, some synthesis products are listed as having been isolated as a residue. It will be understood by one of ordinary skill in the art that the term "residue" does not limit the physical state in which the product was isolated and may include, for example, a solid, oil, foam, a gum, syrup, and the like.

The process to produce Apixaban comprises processes to produce compounds of the formula (8), (10), (11), (16), (17), (18), (21), (23), (24) and (25) as described above and is schematically represented as below:

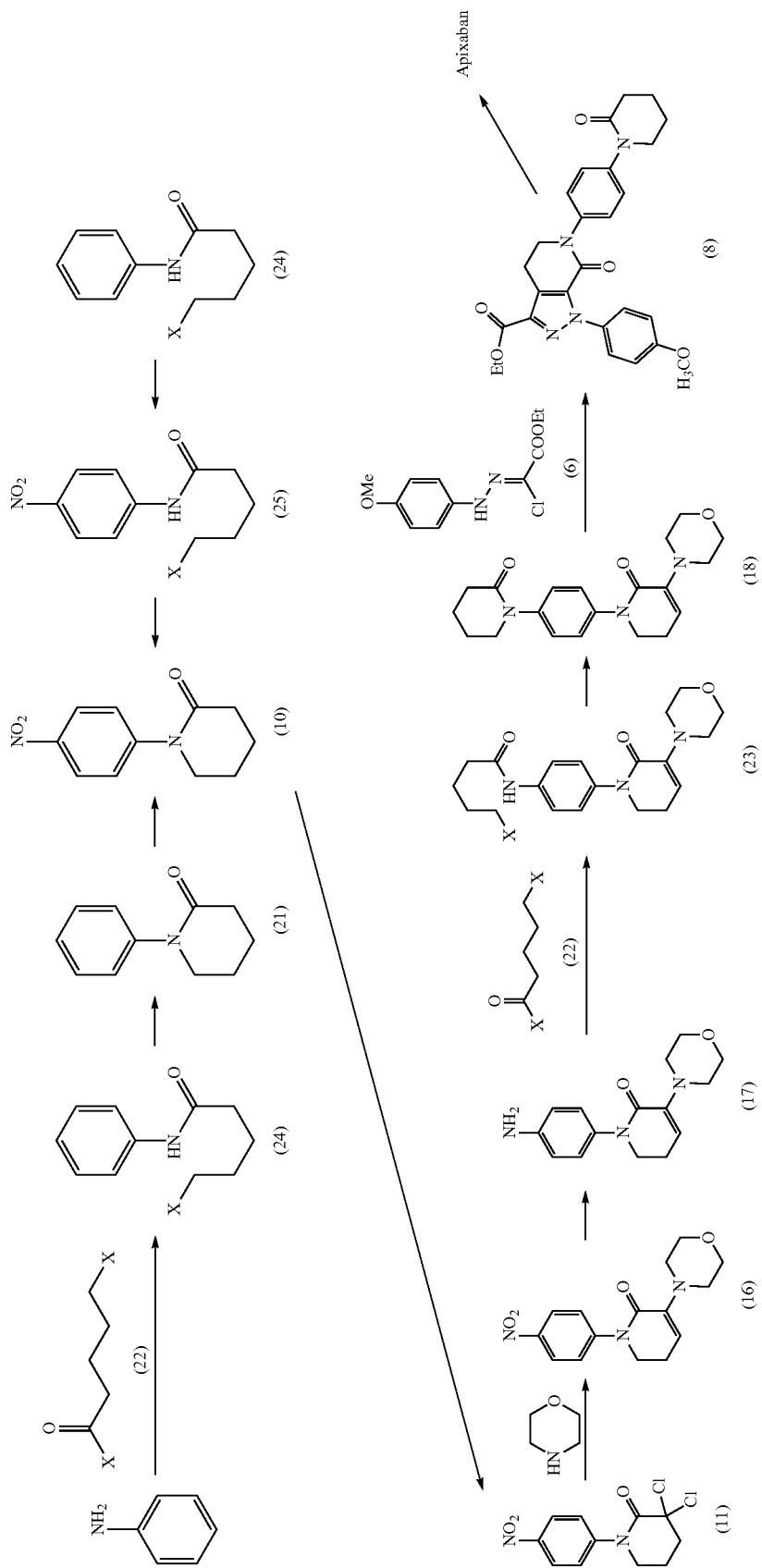

The following examples are set forth to aid the understanding of the invention, and should not be construed to limit in any way the invention set forth in the claims which follow thereafter. The present invention provides process for preparation of Apixaban which is devoid of Ullmann reaction.

EXAMPLES

Example—I: Synthesis of 5-Chloro-pentanoic Acid Phenylamide (24)

A solution of 5-chlorovaleroyl chloride (CVC, 174 gm, 1.12 mol) in methylene dichloride (MDC) (100 ml) added to the suspension of aniline (100 gm, 1.07 mol), sodium hydroxide (52 gm, 1.3 mol), TBAB (2 gm) in MDC (900 ml) and Water (112 ml) at 0-5° C. over 1 hrs and was slowly brought to 25 to 30° C. Organic layer separated, washed with water (200 ml), dried over anhydrous sodium sulfate and distilled at 50° C. to get a residue. The residue was purified in hexane to get white crystals of 5-Chloro-pentanoic acid phenylamide (24). Yield: 222.4 gm, 97.84%

Example—IA: Synthesis of 1-(phenyl) piperidin-2-one (21)

A solution of 5-chlorovaleroyl chloride (CVC, 174 gm, 1.12 mol) in methylene dichloride (100 ml) was added to the suspension of aniline (100 gm, 1.07 mol), sodium hydroxide (52 gm, 1.3 mol), TBAB (2 gm) in methylene dichloride (900 ml) and Water (112 ml) at 0-5° C. over 1 hrs. The mixture was slowly brought to 25 to 30° C. and then aq. solution of KOH (200 gm, 3.57 mol in 310 ml water) was added slowly in 10-15 min and stirred for 5-6 hrs at room temperature. Organic layer was separated, washed with water (200 ml) and distilled out atmospherically at 50° C. to get a residue. Toluene (200 ml) and Hexane (600 ml) were added to the residue and stirred at same temperature for 30 min. The resulting slurry was gradually cooled to 0-5° C. and filtered. Solid dried at about 50° C. to afford the desired product as white crystals. Yield: 185 g, 97.36% Purity: 99.55% MP-98-100° C.

Example—II: Preparation of 1-(4-Nitrophenyl) piperidin-2-one (10)

Cold nitric acid (70%, 54 g, 0.6 mol) was added drop wise to the precooled solution of example—IA (100 gm, 0.57 mol) in 160 ml of Sulphuric acid at 0-5° C. over 1-2 hrs. After complete addition, reaction mass was quenched over ice-water and stirred for 1 hr. Filtered off solid, washed with cold water (65 ml×3 times), unloaded and dried at 50-60° C. in hot air oven for about 5-6 hrs. Pale yellow solid was obtained. Yield: 100.5 gm, 80%. The product can be optionally purified from IPA to give off white solid.

Example IIA: 5-chloro-N-(4-nitrophenyl) pentanamide (25)

The compound of example IIA were prepared by a method analogous to that described in Example No II by using 5-chloro-N-phenylpentanamide as a Starting material.

Example—IIB: Preparation of 1-(4-Nitrophenyl) piperidin-2-one (10)

To the suspension of compound 25 (50.0 gm, 0.195 mol) in 300 ml THF, was added TBAB (1.0 gm)&aqueous solution of KOH (43.68 gm, 0.78 mol) at 0-10° C. and stirred for 10-12 hrs at room temperature. After completion of reaction THF was evaporated and cold water and ethyl acetate were added. Organic layer was separated, washed with water (200 ml) and distilled out atmospherically at 50° C. to get a residue. Isopropyl alcohol was added and the resulting crystals was gradually cooled to 0-5° C. and filtered. Solid dried at about 50° C. to afford the desired product as off white crystalline solid. Yield: 47.2 g, 75.2%; Purity: 97.55%.

Example—III: Synthesis of 3-Morpholino-1-(4-Nitrophenyl)-5,6-dihydro pyridin-2(1H)-one (16)

$PCl_5$ (212.5 g, 1.02 mol) was slowly added to a solution of the product of example—II (75 g, 0.340 mol) in Toluene (225 mL) at 25-30° C. The resulting mixture was gradually heated to 75-80° C. for 1 h and poured into ice water (1 L), maintaining temperature below 10° C. The quenched mass was stirred at 0-5° C. for 1 h and filtered under suction. The pale yellow colored product was dried in air oven at 55°–60° C. for 6-8 hrs. The dried product was dissolved in DMF (130 ml) and morpholine (130 ml) and refluxed for 1 h. The reaction mixture was cooled to 60° C. and water was added to the reaction mass at the same temperature. The resulting slurry was filtered under suction, washed with water to get a yellow solid. Recrystallization of the solid from MeOH afforded the desired product as an off-white solid. Yield: 85.73 g, 83.0%; MP 158-160° C.

Example—IV: 1-(4-Aminophenyl)-3-morpholino-5, 6-dihydropyridin-2(1H)-one (17)

Hydrazine hydrate 80% (60 gm, 1.19 mol) was added drop wise at around 60-65° C. to the solution containing product of example—III (50 gm, 0.16 mol), Raney nickel (1 gm, 2%) in EtOH (750 ml) and water (150 ml). After completion of addition, stirred for 30 min at same temperature and brought to room temperature. The reaction mass was filtered through celite bed, concentrated under vacuum, added EtOAc (100 ml) and filter under suction. Dried the wet cake in air oven to afford the desired product as a cream colored solid. Yield: 43 gm; 95.55%

Example—V: Synthesis of 5-Chloro-pentanoic Acid [4-(5-morpholin-4-yl-6-oxo-3,6-dihydro-2H-pyridin-1-yl)-phenyl]-amide (23)

A solution of 5-chlorovaleroyl chloride (CVC, 82 gm, 0.5273 mol) in MDC (100 ml) was added to the suspension of product of example—IV (125 gm, 0.4573 mol), sodium hydroxide (22 gm, 0.55 mol), TBAB (3.75 gm) in MDC (1150 ml) and Water (49 ml) at 0-5° C. over 1 hrs. The mixture was slowly brought to 25 to 30° C., 300 ml water was added to the reaction mass and stirred for 10 min. Organic layer was separated and washed with water (200 ml), dried over anhydrous sodium sulfate and distilled atmospherically at 50° C. to get a residue. The residue was purified in EtOAc to get pale yellow solid. Yield: 172 gm, 96.08%

Example—VA: Synthesis of 3-Morpholino-1-(4-(2-oxopiperidin-1-yl)phenyl)-5,6-dihydro pyridin-2 (1H)-one (18)

A solution of 5-chlorovaleroyl chloride (CVC, 82 gm, 0.5273 mol) in MDC (100 ml) was added to the suspension of product of example—IV (125 gm, 0.4573 mol), sodium hydroxide (22 gm, 0.55 mol), TBAB (3.75 gm) in MDC (1150 ml) and Water (49 ml) at 0-5° C. over 1 hr. The mixture was slowly brought to 25 to 30° C., and then the aq. solution of KOH (187 gm, 3.33 mol in 311 ml water) was added slowly in 10-15 min and stirred for 8-10 hrs at room temperature. 300 ml water was added to the reaction mass and stirred for 10 min. Organic layer was separated, washed with water (300 ml) and distilled at 50° C. to get a solid product. Recrystallization of the solid from EtOAc afforded the desired product as a buff colored solid. Yield: 153 gm, 94.27% Purity: 98+%; MP 204-206° C.

Example—VI: (Z)-Ethyl 2-Chloro-2-(2-(4-methoxyphenyl) hydrazono)acetate (6)

Hydrochloric acid (35-36%, 60 ml, 0.6 mol) was added to a solution of 4-methoxyaniline (24.6 g, 0.2 mol) in water (120 ml) at −5 to 0° C. A solution of sodium nitrite (16.6 g, 0.24 mol) in water (80 mL) was added to the mixture drop wise below 0° C. Then, the reaction solution was stirred for 30 min at 0° C., followed by the addition of sodium acetate (32.8 g, 0.40 mol) until pH 5-6. To this, a solution of ethyl 2-chloroacetoacetate (28 mL, 32.8 g, 0.2 mol) in MeOH (300 mL) was added drop wise maintaining temperature between 0-5° C. The resulting solution was stirred at 25-30° C. for 4-6 h; concentrated in vacuum at low pressure, and the residue so obtained was dissolved in water (100 mL) and EtOAc (200 ml). Organic layer was separated. Aqueous phase was extracted with EtOAc (2×100 ml). The combined organic phase was washed with water (2×100 ml) and brine (2×100 ml), dried over anhydrous sodium sulfate, filtrated, and concentrated till residual stage. Recrystallization of the product from EtOAc afforded the pure product as a pale yellow solid. Yield: 39.4 g, 77%

Example—VII: Ethyl-1-(4-Methoxyphenyl)-7-oxo-6-(4-(2-oxopiperidin-1-yl) phenyl)-4,5,6,7-tetrahydro-1H-pyrazolo[3,4-c]pyridine-3-carboxylate (8)

Product of example—VA (14.2 g, 0.04 mol), TEA (17 mL, 0.12 mol), and potassium iodide (KI) (0.64 g, 0.004 mol) were added to a solution of the product of example—VI (11.3 g, 0.044 mol) in EtOAc (200 mL) at room temperature. The mixture was stirred for 6 h under reflux and then cooled to 0° C. To the resulting mixture was added 4.0N hydrochloric acid (50 mL, 0.02 mol) drop wise and stirred at room temperature for 2 h. Thereafter water (100 mL) was added to the mixture to separate the organic layer. The aqueous layer was extracted with EtOAc (3×100 mL), and then the combined organic extracts were washed with brine (2×100 mL), dried over anhydrous sodium sulfate, and concentrated to dryness. Recrystallization of the residue from EtOAc and drying in vacuum afforded as cream colored solid. Yield: 14.6 g, 75%

Example—VIII: Synthesis of Ethyl-1-(4-Methoxyphenyl)-7-oxo-6-(4-(2-oxopiperidin-1-yl) phenyl)-4,5,6,7-tetrahydro-1H-pyrazolo[3,4-c]pyridine-3-carboxylate (8)

Product of example—VA (14.2 g, 0.04 mol), TEA (17 mL, 0.12 mol), and KI (0.64 g, 0.004 mol) were added to a solution of the product of example—VI (11.3 g, 0.044 mol) in MDC (80 mL) at room temperature. The mixture was stirred at 42-45° C. for 12-15 hrs and then cooled to 0° C. To the resulting mixture was added 4.0N hydrochloric acid (50 mL, 0.02 mol) drop wise and stirred at room temperature for 2-4 hrs. Thereafter water (100 mL) was added to the mixture to separate the organic layer. The aqueous layer was extracted with MDC, 50 mL and then the combined organic extracts were washed with brine (2×100 mL), and concentrated to dryness. Recrystallization of the residue from EtOAc and drying in vacuum afforded product as cream colored solid. Yield: 16.58 g, 85%. Purity: 99.5+%

Example—IX: Synthesis of Compound of Formula (I): 1-(4-Methoxyphenyl)-7-oxo-6-(4-(2-oxopiperidin-1-yl)phenyl)-4,5,6,7-tetrahydro-1H-pyrazolo[3,4-c]pyridine-3-carboxamide:[Apixaban] (1)

The Mixture of product of example—VIII (25 g, 0.051 mol) and Methanolic solution of ammonia (200 ml, 15-18%, w/w) were heated at 65-70° C. in a Autoclave for 24 hrs. The solvent was evaporated under low pressure and solid residue obtained was suspended in 175 ml water and left under stirring for 2 hr. solid filtered through Buchner funnel and washed with water (50 ml×2), dried in vacuum at 60° C. to afford the desired product. Yield: 21.5 g, 91.48%;

Example—X: Preparation of Apixaban of Formula (I), Crystalline Form N-1

The obtained Apixaban (25 gm) was dissolved in mixture of MeOH and DMF [(7:3), 650 ml] at about 70° C. After cooling the reaction mass the crystallized product was collected by filtration and dried under vacuum at 70° C. for 12 hrs to afford 20 gm Apixaban. XRPD: main peaks in 2θ: 8.4, 10.0, 10.50, 11.2, 12.3, 12.8, 13.9, 15.16, 16.2, 16.9, 18.4, 18.8, 19.5, 21.1, 21.5, 22.2, 24.7, 25.3, 25.9, 26.9, 27.7, 28.6, 29.2, 29.9, 30.6, 31.7, 32.7 and 34.9° in 2 theta value. As in FIG. 1.

Example—XI: Preparation of Apixaban of Formula (I), Crystalline Form N-1

Apixaban (25 gm) was dissolved in DMF (200 ml) at a temperature of about 70-75° C. To this water (300 ml) was added as anti-solvent. The product crystallized was collected by filtration and dried under vacuum at 70° C. for 12 hrs to afford 22.5 gm Apixaban. Purity: 99.7+%, single max impurity NMT 0.05 w/w. XRPD: main peaks in 2θ: 8.4, 10.0, 10.50, 11.2, 12.3, 12.8, 13.9, 15.16, 16.2, 16.9, 18.4, 18.8, 19.5, 21.1, 21.5, 22.2, 24.7, 25.3, 25.9, 26.9, 27.7, 28.6, 29.2, 29.9, 30.6, 31.7, 32.7 and 34.9° in 2 theta value. As in FIG. 1.

Example—XII: Synthesis of 5-Chloro-pentanoic Acid Phenylamide (24)

A solution of 5-chlorovaleroyl chloride (CVC, 520 gm, 3.35 mol) in methylene dichloride (400 ml) was added to the suspension of aniline (250 gm, 2.68 mol), potassium hydroxide (165 gm, 3.06 mol) and TBAB (2.5 gm) in methylene dichloride (2.1 L) and water (412 ml) at 0-10° C. over a period of 2 hrs. The reaction mixture was then stirred at room temperature for 1 hr; organic layer was separated, washed with water (1 L), dried over anhydrous sodium sulfate and distilled atmospherically at 50° C. to get a residue. The residue was purified in hexane to give white crystals.

Yield: 539.87 gm, 95.15%.

Example—XIII: Synthesis of 5-Chloro-pentanoic Acid Phenylamide (24) in the Absence of any Base and PTC A solution of 5-chlorovaleroyl chloride (CVC, 174 gm, 1.12 mol) in methylene dichloride (MDC, 100 ml) was added to the solution of aniline (100 gm, 1.07 mol), in MDC (900 ml) at 0-5° C. over a period of 1 hr and was slowly brought to 25 to 30° C. Water (500 ml) was added and the mixture was stirred for 5-10 min. Organic layer was separated, washed with water (200 ml), dried over anhydrous sodium sulfate and distilled at 50° C. to get a residue. The residue was purified in hexane to get white crystals of 5-Chloro-pentanoic acid phenyl amide (24). Yield: 199.4 gm, 87.75%.

Example—XIV: Synthesis of 1-(phenyl) piperidin-2-one (21) without isolation of (24)

A solution of 5-chlorovaleroyl chloride (CVC, 174 gm, 1.12 mol) in methylene dichloride (MDC, 100 ml) was added to the solution of aniline (100 gm, 1.07 mol), in MDC (900 ml) at 0-5° C. over a period of 1 hr and was slowly brought to 25 to 30° C. and then aq. solution of KOH (200 gm, 3.57 mol in 310 ml water) was added slowly in 10-15 min, charged TBAB (2 gm) and stirred for 5-6 hrs at room temperature. Organic layer was separated, washed with water (200 ml) and distilled out atmospherically at 50° C. to get a residue. Toluene (200 ml) and hexane (600 ml) were added to the residue and stirred at same temperature for 30 min. The resulting slurry was gradually cooled to 0-5° C. and filtered. Solid dried at about 50° C. to afford the desired product as white crystals. Yield: 165.8 g, 87.26%; Purity: 99.2%; MP: 98-100° C.

Example—XV: Synthesis of 1-(phenyl) piperidin-2-one (21)

A solution of 5-chlorovaleroyl chloride (CVC, 520 gm, 3.35 mol) in methylene dichloride (400 ml) was added to the suspension of aniline (250 gm, 2.68 mol), potassium hydroxide (450 gm, 8.35 mol) in methylene dichloride (2.1 L) and DMF (500 ml) at 0-10° C. over a period of 2 hrs. The mixture was slowly brought to 25 to 30° C. and stirred overnight under $N_2$ atmosphere. The reaction mass was then quenched with chilled water (1.5 L) below 10° C. Organic layer was separated, washed with water (1 L), dried over anhydrous sodium sulfate and distilled atmospherically at 50° C. to get a residue. To the residue was added toluene (400 ml) and stirred at same temperature for 30 min. The resulting suspension was gradually cooled to 0-5° C. and filtered. Solid was dried at about 50° C. to afford the desired product as white crystals. Yield: 400 g, 85.15%; MP: 98-100° C.

Example—XVI: Synthesis of 1-(phenyl) piperidin-2-one (21)

A solution of 5-chlorovaleroyl chloride (CVC, 174 gm, 1.12 mol) in methylene dichloride (100 ml) was added to the suspension of aniline (100 gm, 1.07 mol), sodium hydroxide (52 gm, 1.3 mol), TBAB (2 gm) in methylene dichloride (900 ml) and Water (112 ml) at 0-5° C. over a period of 1 hr. The mixture was slowly brought to 25 to 30° C. and added 200 ml water stirred for 5-10 min. Separated organic layer was added drop wise to the suspension of KOH (121 gm, 2.16 mol) in 300 ml DMF under nitrogen atmosphere at 0-10° C. and stirred for 2-4 hrs at room temperature. Reaction mass was quenched using cold water, organic layer was separated, washed with water (200 ml) and distilled out atmospherically at 50° C. to get a residue. Toluene (200 ml) and hexane (600 ml) were added to the residue and stirred at same temperature for 30 min. The resulting slurry was gradually cooled to 0-5° C. and filtered. Solid dried at about 50° C. to afford the desired product as white crystals. Yield: 161.5 g, 85.3%. Purity: 98.55%; MP: 98-100° C.

Example—XVII: Synthesis of 1-(phenyl) piperidin-2-one (21)

To the suspension of KOH (53 gm, 0.947 mol) in 100 ml DMF and 900 ml MDC, compound 24 (100 gm, 0.473 mol) was added lot wise under nitrogen atmosphere at 0-10° C. and stirred for 2-4 hrs at room temperature. Reaction mass was quenched using cold water and Organic layer was separated, washed with water (200 ml) and distilled out atmospherically at 50° C. to get a residue. Toluene (200 ml) and hexane (600 ml) were added to the residue and stirred at same temperature for 30 min. The resulting slurry was gradually cooled to 0-5° C. and filtered. Solid dried at about 50° C. to afford the desired product as white crystals. Yield: 70.49 g, 85.3%; Purity: 98.73%; MP: 98-100° C.

Example—XVIII: Synthesis of 5-Chloro-pentanoic Acid [4-(5-morpholin-4-yl-6-oxo 3,6-dihydro-2H-pyridin-1-yl)-phenyl]-amide (23) in Absence of Base A solution of 5-chlorovaleroyl chloride (CVC, 16.4 gm, 0.10 mol) in MDC (20 ml) was added to the suspension of compound 17 (25 gm, 0.09 mol), in MDC (230 ml) at 0-5° C. over a period of 1 hr. The mixture was slowly brought to 25 to 30° C., 300 ml water was added and stirred for 10 min. Organic layer was separated and washed with water (40 ml), dried over anhydrous sodium sulfate and distilled atmospherically at 50° C. to get a residue. The residue was purified using ethyl acetate to get compound 23 as pale yellow solid. Yield: 26.85 gm, 75%.

Example—XIX: Synthesis of 3-Morpholino-1-(4-(2-oxopiperidin-1-yl) phenyl)-5,6-dihydro pyridin-2 (1H)-one (18) in Absence of PTC A solution of 5-chlorovaleroyl chloride (14.1 gm, 0.09 mol) in MDC (10 ml) was added to a mixture containing compound 17 (20 gm, 0.07 mol) and KOH (12.29 gm, 0.22 mol) in MDC (200 ml) and DMF (40 ml) below 10° C. The mixture was slowly brought to ambient temperature and stirred under $N_2$ for 3-5 hrs. The reaction mass was cooled to 10-15° C., quenched with water, stirred and the layers were separated. The organic layer was concentrated under vacuum and dried to afford desired compound 18 as a cream colored solid. Yield: 22.10 g, 85%; MP: 204-206° C.

The invention claimed is:
1. A process for preparation of lactam compound of formula (18) comprising steps of;
   a. reacting amino-morpholine compound of formula (17) with compound of formula (22) in presence of inorganic base or aqueous solution of inorganic base or absence of any base optionally in presence of phase transfer catalyst to obtain amide-compound of formula (23), wherein X is leaving group;
   b. optionally isolating the amide-compound of formula (23); and c. cyclizing amide-compound of formula (23) in presence of inorganic base or aqueous solution of inorganic base optionally in presence of phase transfer catalyst to obtain a lactam compound of formula (18).

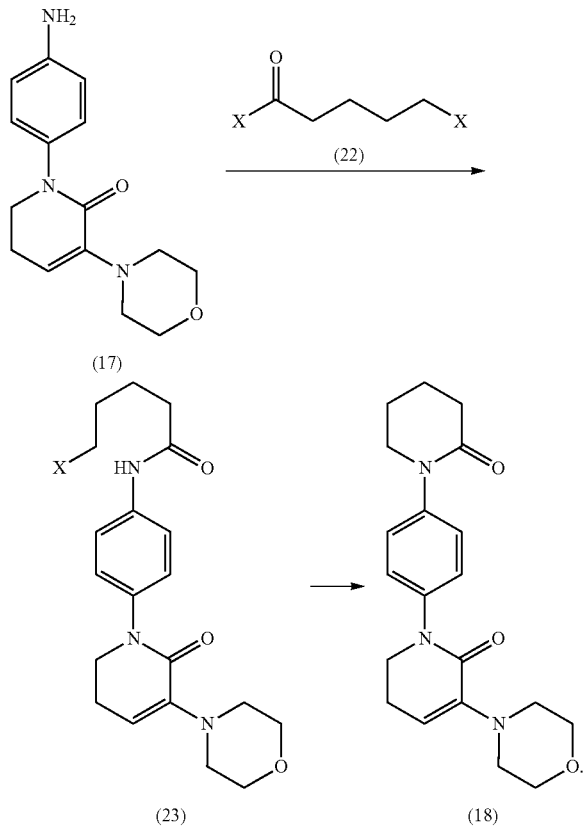

2. The process according to claim 1, wherein inorganic base is selected from the group consisting of sodium carbonate, potassium carbonate, lithium carbonate, lithium hydroxide, sodium hydroxide, potassium hydroxide, ammonium hydroxide, lithium hydrate, potassium hydrate, sodium hydrate, lithium hydrogen carbonate, sodium hydrogen carbonate, potassium hydrogen carbonate, and mixture(s) thereof.

3. The process according to claim 1, wherein step (a) and step (c) are carried out in presence of a solvent selected from the group consisting of methylene dichloride (MDC), toluene, ethyl acetate, methyl acetate, $CHCl_3$, chlorobenzene, dimethylformamide (DMF), dimethylacetamide, N-methylpyrrolidone, acetonitrile, dimethyl sulfoxide, tetrahydrofuran (THF), dioxane and mixture(s) thereof.

4. The process according to claim 1, wherein the phase transfer catalyst is selected from the group consisting of methyltridecyl ammonium chloride, trimethyl ammonium chloride, tetrabutylammonium bromide, dimethylethylhexadecyl ammonium bromide, ethyltripentyl ammonium iodide, benzyltrimethylammonium chloride, and hexadecyltributylphosphonium bromide.

5. The process according to claim 1, wherein leaving group is selected from the group consisting of Cl, Br, I, F, mesylate, triflate, tosylate and tert-butyldimethylsilyloxy group.

* * * * *